United States Patent [19]

Bjorklund et al.

[11] Patent Number: 4,523,847
[45] Date of Patent: Jun. 18, 1985

[54] FREQUENCY MODULATION-POLARIZATION SPECTROSCOPY METHOD AND DEVICE FOR DETECTING SPECTRAL FEATURES

[75] Inventors: Gary C. Bjorklund, Los Altos; Marc D. Levenson, Saratoga, both of Calif.

[73] Assignee: International Business Machines Corporation, Armonk, N.Y.

[21] Appl. No.: 511,593

[22] Filed: Jul. 7, 1983

[51] Int. Cl.³ .............................................. G01B 9/02
[52] U.S. Cl. ................................... 356/349; 356/351; 356/364
[58] Field of Search ................ 356/349, 351, 364, 368

[56] References Cited

U.S. PATENT DOCUMENTS 4,297,035 10/1981 Bjorklund .......................... 356/402

OTHER PUBLICATIONS

Azzam, "Frequency-Mixing Detection (FMD) of Polarization-Modulated Light", *J. Opt. Soc. Am.*, vol. 66, No. 7, pp. 735-739, 7/76.

*Primary Examiner*—Davis L. Willis
*Assistant Examiner*—Matthew W. Korey
*Attorney, Agent, or Firm*—Joseph E. Kieninger

[57] ABSTRACT

A method and device for detecting dichroic and/or birefringent narrow spectral features in a sample is described. The method includes the steps of providing a beam of light having an optical frequency bandwidth which is narrow compared to the width of the narrow spectral feature and having a center frequency $\omega_c$ which lies near the narrow spectral feature, polarization phase modulating a beam of light with a single RF frequency to provide a pure FM spectrum having upper and lower sidebands in which either the carrier and sidebands have been polarized with respect to one another, exposing the sample containing the narrow spectral feature to the polarized modulated light so that the FM sidebands probe the narrow spectral feature, polarization analyzing and then photodetecting the light emerging from the sample to detect a RF beat at the specific RF frequency used for the polarization phase modulation, and electronically monitoring the amplitude of the RF beat signal to indicate the strength of the narrow spectral feature. The device includes a polarization phase modulator and a polarization analyzer positioned on opposite sides of the sample. In a preferred embodiment the polarization phase modulator produces a frequency modulated optical spectrum with the sidebands polarized precisely orthogonal to the carrier.

11 Claims, 9 Drawing Figures

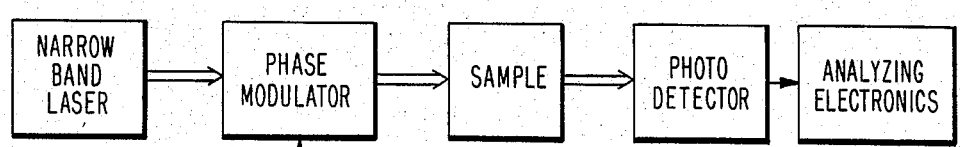
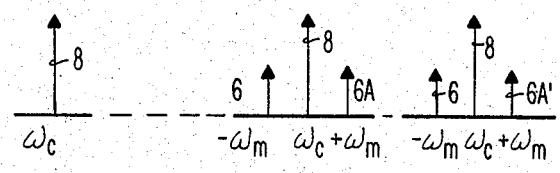
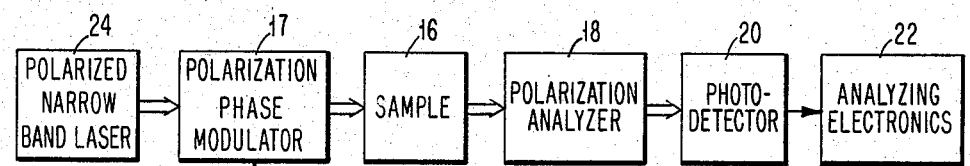
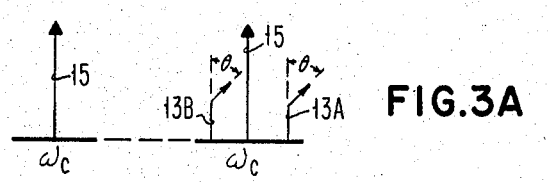
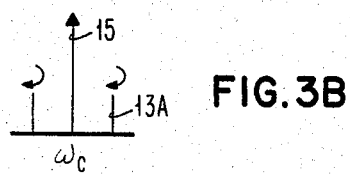
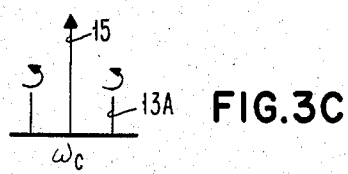
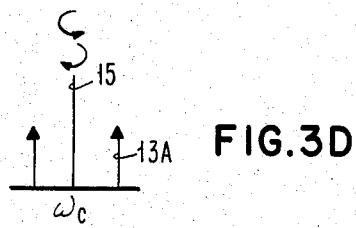

FREQUENCY MODULATION-POLARIZATION SPECTROSCOPY METHOD AND DEVICE FOR DETECTING SPECTRAL FEATURES

DESCRIPTION

1. Technical Field

This invention relates to spectroscopy and more particularly to a method and apparatus utilizing frequency modulation-polarization spectroscopy for detecting one or more polarization anistropic spectral features in a sample.

2. Background Art

Polarization spectroscopy has shown considerable promise as a sensitive tool for high resolution laser spectroscopy. Polarization spectroscopy has the advantage of allowing adjustable optical intensity and of minimal perturbation of the sample since the intense local oscillator beam is polarized orthogonal to the probe beam. However, polarization spectroscopy suffers from the disadvantage of sensitivity to low frequency laser power fluctuations from flicker or 1/f noise and from the disadvantage of being sensitive to background birefringence.

Frequency modulation (FM) spectroscopy as described in the patent to Bjorklund U.S. Pat. No. 4,297,035 and assigned to the assignee of the present invention, has also shown considerable promise as sensitive tool for high resolution laser spectroscopy. This patent is included in this application by reference thereto. The apparatus for FM spectroscopy is shown in FIG. 1. The phase modulator provides two balanced sidebands 6 as shown in Fig. 1A. The polarization of the sidebands 6 is always parallel to the carrier frequency component 8. When this modulated beam passes through the sample one of the sidebands 6A probes the narrow spectral feature and becomes unbalanced sideband 6A'. This difference in the sidebands is detected in the photodetector to produce an RF beat signal which is monitored by the analyzing electronics.

The primary advantage of FM spectroscopy is a zero background, that is, a signal only appears when the sidebands are unbalanced. In addition, only an FM spectrum is useful for this purpose since the other spectrums give non-zero background, that is, noise. FM spectroscopy, however, has three disadvantages. One disadvantage is that there is a residual amplitude modulation (AM) produced because the phase modulator and other optical elements are imperfect and this results in some background noise. A second disadvantage is that the carrier $\omega_c$ is strong compared with the sidebands and as a result is destructive to the sample. This is a particularly serious problem when FM spectroscopy is used in holeburning memories. The third disadvantage is that FM spectroscopy is insensitive to polarization anisotropy, that is, birefringence, dichroism, and optical activity.

SUMMARY OF THE INVENTION

It is a primary object of this invention to provide an improved method and apparatus for detecting a single narrow anisotropic spectral feature.

It is another object of this invention to provide an improved frequency modulation spectroscopy method and apparatus having a low level of background noise.

It is still another object of this invention to provide an improved frequency modulation spectroscopy method and apparatus in which the carrier $\omega_c$ is not destructive.

It is a further object of this invention to provide an improved frequency modulation spectroscopy method and apparatus that is sensitive to birefringence, dichroism, and optical activity.

These and other objects are accomplished through a FM-polarization spectroscopy method and device for detecting dichroic and/or birefringent narrow spectral features in a sample. The method includes the steps of providing a beam of light having an optical frequency bandwidth which is narrow compared to the width of the narrow spectral feature and having a center frequency $\omega_c$ which lies near the narrow spectral feature, polarization phase modulating a beam of light with a single RF frequency to provide a pure FM spectrum having upper and lower sidebands in which either the carrier and/or sidebands have been produced in different states of polarization, exposing the sample containing the narrow spectral feature to the FM polarization-modulated light so that the FM sidebands probe the narrow spectral feature, polarizing and then photodetecting the light emerging from the sample to detect a RF beat at the specific RF frequency used for the polarization phase modulation, and electronically monitoring the amplitude of the RF beat signal to indicate the strength of the narrow spectral feature. The device includes a polarization phase modulator and a polarization analyzer positioned on opposite sides of the sample. The sidebands may be linearly polarized at an angle $\theta$ with respect to the carrier where $\theta$ is any angle between 0° and 90°. In a preferred embodiment the polarization phase modulator produces a frequency modulated optical spectrum with the sidebands polarized precisely orthogonal to the carrier ($\theta = 90°$). The sidebands may also be polarized circularly in a counterclockwise or clockwise manner. Similarly the carrier may be polarized circularly in the same manner.

Other objects of this invention will be apparent from the following detailed description, reference being made to the following drawings in which specific embodiments of the invention are shown.

BRIEF DESCRIPTION OF THE DRAWINGS

FIG. 1 is a schematic diagram of a prior art FM spectroscopy device;

FIG. 1A is a diagram showing the carrier and the FM sidebands of the device shown in FIG. 1;

FIG. 3 is a schematic diagram of the device in accordance with this invention;

FIG. 3A through 3D illustrates examples of the polarization states of the FM sidebands and carrier obtained with the device of FIG. 2.

DESCRIPTION OF THE PREFERRED EMBODIMENT

Figure 2:
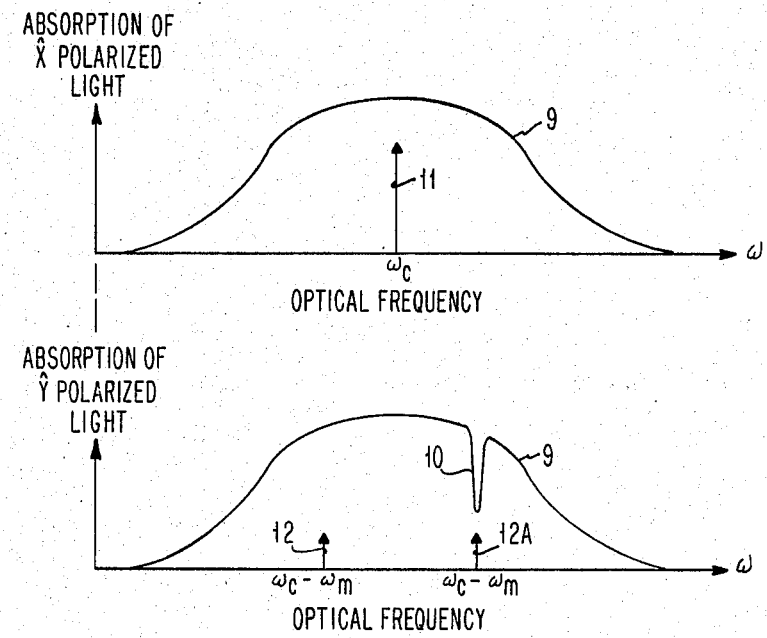
FIG. 2 shows an anisotropic photochemical hole burned in an inhomogeneous absorption band.

An embodiment will now be described in terms of the device and method for the readout of information encoded by the presence or absence of anisotropic photochemical holes burned in an inhomogeneous absorption band of a sample as shown in FIG. 2. The inhomogeneous absorption band 9 is the same for both x and y polarized light. The anisotropic photochemical hole 10 only affects y polarized light. The FM polarization modulated laser beam consists of a carrier component 11 at optical frequency $\omega_c$ polarized in the x direction and of two sidebands 12 and 12A at respective optical frequencies $\omega_c - \omega_m$ and $\omega_c + \omega_m$ polarized in the y direction. The laser beam is assumed to propagate in the z direction (not shown). As shown in FIG. 3, the first step is to provide a linearly polarized narrow band laser 24 having an optical frequency $\omega_c$. Examples of a narrow band laser are a single frequency dye laser and a fixed single mode frequency solid state laser. The carrier frequency 15, $\omega_c$, as shown in FIG. 3A, is chosen to lie within the inhomogeneous absorption band of the sample 16. An inhomogeneous absorption band with anisotropic holes is one example of a spectral feature whose dichroism and/or birefringence vary with optical frequency. The laser has a band which is narrow compared with the desired resolution of the information and the spectral feature, that is, for example, the width of a photochemical hole.

The laser passes light into the polarization phase modulator 17 which polarizes and modulates the light from the laser source to provide FM sidebands 13A and 13B.

Electronic means 14 drives the polarization phase modulator 17 simultaneously with a single RF frequency to reproduce light with FM sidebands in a different state of polarization than the carrier. An example of such an electronic means 14 is an RF oscillator.

This laser beam may have the sidebands polarized an angle of $\theta$ with respect to the carrier as shown in FIG. 3A. As shown in FIG. 3B, the sidebands 13 are circular in a clockwise direction. In FIG. 2C the sidebands 13 are circular in a counterclockwise direction. In FIG. 3D the carrier 15 is circularly polarized whereas the sidebands are linearly polarized. While four different combinations of polarized carriers and sidebands have been shown in FIGS. 3A through 3D, it is understood that other combinations may be used. FIGS. 3A–3D show that this invention covers all types of linear and circular polarizations. It also includes elliptical polarizations. In these cases, the polarization analyzer 18 can be oriented to transmit only a portion of the carrier and none of the sidebands or only a portion of the sidebands and none of the carrier. Resonances with anisotropic spectral features alter these polarization transmission/rejection conditions to produce a beat frequency at the photodetector 20.

A bit of information in the sample 16 is encoded by the presence or absence of an anisotropic hole at a location which corresponds to a particular FM upper sideband. The presence of a hole will cause a differential polarization change, absorption or phase shift to be experienced between the upper FM sideband 13A and the lower FM sideband 13B which correspond to the hole location. Such a differential will produce a heterodyne amplified beat signal with the corresponding RF frequency at the photodetector 20 after it has passed through the polarization analyzer 18. If there is no differential, no beat signal will be produced.

An example of a photodetector 20 is a solid state PIN diode. The design of electronics 22 is straightforward and well within the state of the art. An example of the electronics 22 is a double balanced mixer, which is driven by a local oscillator at the RF frequency used to modulate the laser.

The analyzing electronics 22 isolates the signals due to the differential absorption from those due to the differential phase shift by comparing the phase of the RF beat signal to the phase of the corresponding RF driving frequency of the modulator. If there are a large number of hole locations, it is advantageous to use only that portion of the beat signal which is due to the differential absorption, since the combined phase differentials caused by the presence of the holes at other frequency locations can cause a spurious differential signal. The length of the time necessary for the readout is of the order of $\Delta\omega^{-1}$, where $\Delta\omega$ is the typical frequency spacing between hole locations.

Figure 4:
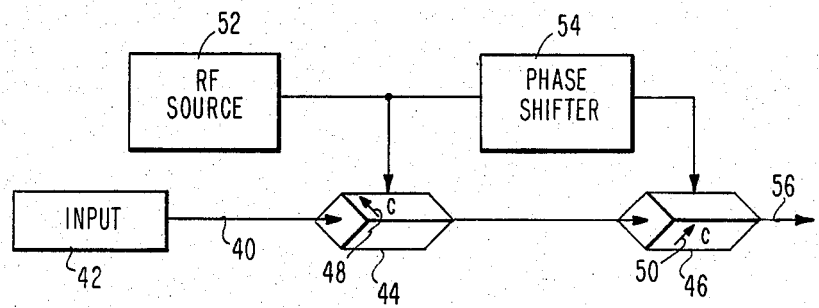
FIG. 4 is one particular example of a polarization phase modulator capable of producing the polarization condition of FIG. 3A with $\theta = 90°$.

An example of a polarization phase modulator 17 is shown in FIG. 4. The linearly polarized beam (40) from the narrow bend laser (42) is incident on two electro-optic phase modulators (44) and (46) with optical axes (c axes) (48) and (50) respectively, orthogonal to one another. The applied RF electric field direction is always parallel to the C axis of each crystal. The angle between the direction of polarization of the linearly polaried beam (40) and the optical axis of the first modulator is 45°. Both phase modulators are driven by the same RF source (52), but a phase shifter (54) allows the relative phases of the RF waveforms driving the crystals to be adjusted to arbitrary value. This phase is adjusted until the sidebands produced by the two crystals cancel in the initial polarization direction while at the same time adding constructively in the direction orthogonal to the initial polarization direction. The emerging beam (56) thus has a carrier $\omega_c$ polarized in the same direction as the original beam and sidebands polarized orthogonal to the carrier.

By using this method and/or device, all of the advantages found with a FM spectroscopy device are retained. In addition, a number of the disadvantages of the prior art system are eliminated. For example, a residual amplitude modulation (AM) produced because the phase modulator and other optical elements are imperfect resulting in background noise, is no longer a problem due to the fact that the polarization analyzer can be oriented to totally reject all sideband light which is not perturbed by the sample. Another advantage of this device is that the carrier $\omega_c$ is no longer destructive to the information provided by the sidebands. Whereas in FM spectroscopy a carrier $\omega_c$ is strong to such an extent that it can perturb the sample. This particular advantage is particularly useful for holeburning memories. A third advantage is that this method is sensitive to polarization anisotropy, that is, birefringence, dichroism, or optical activity. The FM polarization spectroscopy method and device described herein retains the advantages of FM spectroscopy while at the same time it does not have the disadvantages associated therewith.

This method and device is also useful for those applications where polarization spectroscopy has been heretofore used. In particular, in high resolution spectroscopy (saturation spectroscopy) of gases, an orthogonal carrier polarization permits optical heterodyne detection of anisotropies without power broadening or light shifts. Optical heterodyne detection at an RF frequency also enhances sensitivity in ellipsometry and other classical spectroscopic techniques. The use of the FM polarization spectrum suppresses otherwise troublesome noise signals.

This invention provides a basis for spectrographic diagnostic instruments, for example, for gas phase chemical reaction or molecular beam epitaxy. This invention describes a method for detecting dichroic and/or birefringent spectral features. The first step in this method is providing a narrow beam of light having an optical frequency bandwidth which is narrower than the width of the absorption line and which has a center frequency $\omega_c$. The next step is to polarization phase modulate the beam of light with a single RF frequency to provide a pure FM spectrum having upper and lower sidebands in which the carrier and sidebands have been polarized differently from one another. The sample is exposed to the modulated light so that only one of the FM sidebands probes the absorption line. The light emerging from the sample is then passed through a polarization analyzer to a photodetector to detect an RF beat at the specific RF frequency used for the phase modulation. The amplitude of the RF beat signal is electrically monitored as the sideband frequency is varied to indicate the strength of the absorption line.

This invention also provides a basis for multiplex detection of a plurality of polarization anisotropic spectral features, each located at different optical frequencies. An example of such a plurality of spectral features is a plurality of anisotropic photochemical holes burned into an absorption band. The multiplex detection is accomplished by providing a narrow beam of light having an optical frequency bandwidth which is narrower than the width of the spectral features and which has a center frequency $\omega_c$. The next step is to polarization phase modulate the beam of light with a plurality of RF frequencies to provide a pure FM optical spectrum having a plurality of upper and lower sidebands in which the carrier and sidebands have different states of polarization. The sample is exposed to the modulated light so that each one of the upper FM sidebands probes one of the spectral features. The light emerging from the sample then passed through a polarization analyzer to a photodetector to detect a plurality of RF beats at the specific RF frequencies used for polarization phase modulation. The amplitudes of the RF beast signals are electronically monitored in a multiplex manner to indicate the strength of each of the plurality of anisotropic spectral features.

Although preferred embodiments have been described, it is understood that numerous variations may be made in accordance with the principles of this invention.

We claim:

1. A method of detecting a single, narrow polarization anisotropic spectral feature in a sample comprising
   providing a beam of light having an optical frequency bandwidth which is narrow compared to the width of the narrow spectral feature and having a center frequency $\omega_c$ which lies near the feature,
   polarization phase modulating the beam of light with a single RF frequency to provide a pure FM spectrum having a carrier frequency and upper and lower sidebands where the sidebands and carrier are in different states of polarization,
   exposing the sample containing the narrow spectral feature to the polarized modulated light so that the FM sidebands probe the narrow spectral feature,
   polarization analyzing the light emerging from the sample,
   photodetecting the light from the polarizer to detect a beat at a specific RF frequency used for polarization phase modulation, and
   electronically monitoring the amplitude of the RF beat signal to indicate the strength of the narrow spectral feature.

2. A method as described in claim 1 whereby the carrier is linearly polarized in one direction and both sidebands are linearly polarized in another direction at an angle $\theta$ between 0° and 90° to the first direction.

3. A method as described in claim 2 whereby $\theta$ is exactly 90°.

4. A method as described in claim 1 whereby the sidebands are circularly polarized and the carrier is linearly polarized.

5. A method as described in claim 1 whereby the sidebands are elliptically polarized and the carrier is linearly polarized.

6. A method as described in claim 1 whereby the carrier is circularly polarized and both sidebands are linearly polarized in the same direction.

7. A method as described in claim 1 wherein the carrier is elliptically polarized and both sidebands are linearly polarized in the same direction.

8. A method as described in claim 1 wherein a plurality of narrow polarization anisotropic spectral features are detected using light which is polarization phase modulated with a plurality of RF frequencies and a plurality of RF beat signals at the specific RF frequencies used for phase modulation are electronically monitored in a multiplex manner.

9. A device for detecting a narrow polarization anisotropic spectral feature in a sample comprising
   a laser source having a bandwidth narrower than the width of the narrow spectral feature and having a center carrier frequency $\omega_c$ which lies near a selected narrow spectral feature,
   polarization phase modulator means for modulating the light from said laser source to a pure FM spectrum having upper and lower sidebands,
   means for driving said modulator means with a single RF frequency to produce FM sideband which probe the selected narrow spectral feature in the sample,
   polarizer means for analyzing the light after it has passed through said sample,
   photodetection means to receive the light after it has passed through the polarizer, and
   electronic means which is capable of monitoring the intensity of the RF electrical signals from said photodetection means to indicate the strength of the selected narrow spectral feature.

10. A device as described in claim 8 wherein the polarization phase modulator means includes at least one phase modulator each driven by an RF frequency waveform with independently adjustable phase.

11. A device as described in claim 8 wherein the polarization phase modulator beam consists of two phase modulator crystals with optical axes orthogonal to one another, each crystal driven by an RF frequency waveform with independently adjustable phase, and a polarization comparator.

* * * * *

UNITED STATES PATENT AND TRADEMARK OFFICE
CERTIFICATE OF CORRECTION

PATENT NO. : 4,523,847
DATED : June 18, 1985
INVENTOR(S) : Gary C. Bjorklund and Marc D. Levenson It is certified that error appears in the above—identified patent and that said Letters Patent is hereby corrected as shown below:

IN THE CLAIMS

Column 6, line 55, "claim 8" should be --claim 9--.

Column 6, line 59, "claim 8" should be --claim 9--.

Signed and Sealed this

Twenty-sixth Day of November 1985

[SEAL]

Attest:

DONALD J. QUIGG

Attesting Officer

Commissioner of Patents and Trademarks